United States Patent
Nowlin et al.

(10) Patent No.: US 12,414,828 B2
(45) Date of Patent: *Sep. 16, 2025

(54) TELEOPERATED SURGICAL SYSTEM WITH SURGEON SKILL LEVEL BASED INSTRUMENT CONTROL

(71) Applicant: Intuitive Surgical Operations, Inc., Sunnyvale, CA (US)

(72) Inventors: William C. Nowlin, Los Altos Hills, CA (US); Mahdi Azizian, San Jose, CA (US); Simon P. DiMaio, San Carlos, CA (US); Brian D. Hoffman, Mountain View, CA (US); Anthony M. Jarc, Johns Creek, GA (US); Henry C. Lin, Cupertino, CA (US); May Quo-Mei Liu, Rougemont, NC (US); Ian E. McDowall, San Francisco, CA (US); Brent Tokarchuk, San Carlos, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/416,759

(22) Filed: Jan. 18, 2024

(65) Prior Publication Data
US 2024/0197421 A1      Jun. 20, 2024

Related U.S. Application Data

(63) Continuation of application No. 16/349,202, filed as application No. PCT/US2017/061136 on Nov. 10, 2017, now Pat. No. 11,931,122.
(Continued)

(51) Int. Cl.
*A61B 34/35*      (2016.01)
*A61B 34/00*      (2016.01)
(Continued)

(52) U.S. Cl.
CPC .............. *A61B 34/35* (2016.02); *A61B 34/10* (2016.02); *A61B 34/20* (2016.02); *A61B 34/25* (2016.02);
(Continued)

(58) Field of Classification Search
CPC ........... A61B 2017/00477; A61B 2018/00595; A61B 2018/00988; A61B 2034/101;
(Continued)

(56) References Cited

U.S. PATENT DOCUMENTS 9,026,247 B2      5/2015  White et al.
9,649,164 B2 *    5/2017  Kim ..................... B25J 9/1676
(Continued)

FOREIGN PATENT DOCUMENTS

CN      102525644 A      7/2012
CN      203381739 U      1/2014
(Continued)

OTHER PUBLICATIONS

Chinese Patent Office, First Chinese Office Action for Application No. 201780073370X, mailed Jan. 29, 2022 with English Translation, 30 pages.
(Continued)

*Primary Examiner* — Christopher L Cook
(74) *Attorney, Agent, or Firm* — Foley & Lardner LLP

(57) ABSTRACT

A teleoperated surgical system is provided comprising: a first robotic surgical instrument; an image capture; a user display; a user input command device coupled to receive user input commands to control movement of the first robotic surgical instrument; and a movement controller coupled to scale a rate of movement of the first robotic surgical instrument, based at least in part upon a surgical skill level at using the first robotic surgical instrument of the user providing the received user input commands, from a
(Continued)

rate of movement indicated by the user input commands received at the user input command device.

18 Claims, 11 Drawing Sheets

Related U.S. Application Data

(60) Provisional application No. 62/421,072, filed on Nov. 11, 2016.

(51) Int. Cl.
| | | |
|---|---|---|
| *A61B 34/10* | (2016.01) | |
| *A61B 34/20* | (2016.01) | |
| A61B 17/00 | (2006.01) | |
| A61B 18/00 | (2006.01) | |
| A61B 34/30 | (2016.01) | |
| A61B 90/00 | (2016.01) | |

(52) U.S. Cl.
CPC ........... *A61B 2017/00477* (2013.01); *A61B 2018/00595* (2013.01); *A61B 2018/00988* (2013.01); *A61B 2034/101* (2016.02); *A61B 2034/256* (2016.02); *A61B 2034/302* (2016.02); *A61B 2090/3612* (2016.02); *A61B 2090/364* (2016.02); *A61B 90/37* (2016.02)

(58) Field of Classification Search
CPC ........ A61B 2034/256; A61B 2034/258; A61B 2034/302; A61B 2090/3612; A61B 2090/364; A61B 34/10; A61B 34/20; A61B 34/25; A61B 34/35; A61B 34/74; A61B 34/77; A61B 90/37
See application file for complete search history.

(56) References Cited

U.S. PATENT DOCUMENTS

| | | |
|---|---|---|
| 11,931,122 B2 | 3/2024 | Nowlin et al. |
| 2007/0083098 A1 | 4/2007 | Stern et al. |
| 2007/0172803 A1 | 7/2007 | Hannaford et al. |
| 2010/0234857 A1 | 9/2010 | Itkowitz et al. |
| 2011/0054689 A1 | 3/2011 | Nielsen et al. |
| 2011/0208338 A1 | 8/2011 | Eteminan et al. |
| 2011/0306986 A1 | 12/2011 | Lee et al. |
| 2012/0143182 A1 | 6/2012 | Ullrich et al. |
| 2013/0172908 A1 | 7/2013 | Sang et al. |
| 2014/0051049 A1 | 2/2014 | Jarc et al. |
| 2014/0094968 A1 | 4/2014 | Taylor et al. |
| 2014/0287393 A1 | 9/2014 | Kumar et al. |
| 2014/0378995 A1 | 12/2014 | Kumar et al. |
| 2015/0305936 A1 | 10/2015 | Hajishah et al. |
| 2015/0359597 A1 | 12/2015 | Gombert et al. |
| 2016/0098933 A1 | 4/2016 | Reiley et al. |
| 2016/0183930 A1 | 6/2016 | Herzlinger et al. |
| 2016/0314710 A1 | 10/2016 | Jarc et al. |
| 2016/0331474 A1 | 11/2016 | Lacal et al. |
| 2017/0360522 A1 | 12/2017 | Beira |
| 2018/0032130 A1 | 2/2018 | Meglan |
| 2018/0271603 A1* | 9/2018 | Nir .............. A61B 34/25 |
| 2019/0282311 A1 | 9/2019 | Nowlin et al. |
| 2019/0282312 A1 | 9/2019 | Nowlin et al. |
| 2022/0061933 A1 | 3/2022 | Deboeuf et al. |

FOREIGN PATENT DOCUMENTS

| | | |
|---|---|---|
| CN | 203433729 U | 2/2014 |
| CN | 106054737 A | 10/2016 |
| DE | 102008036290 A1 | 2/2010 |
| JP | H0871072 A | 3/1996 |
| JP | 2009131374 A | 6/2009 |
| JP | 2009142379 A | 7/2009 |
| JP | 2012521568 A | 9/2012 |
| JP | 2014520279 A | 8/2014 |
| KR | 20150027618 A | 3/2015 |
| WO | WO-2016028858 A1 | 2/2016 |
| WO | WO-2016053657 A1 | 4/2016 |

OTHER PUBLICATIONS

Extended European Search Report for Application No. 17869216.6, mailed on Jun. 16, 2020, 7 pages.
International Preliminary Report on Patentability for Application No. PCT/US2017/061136, mailed on May 23, 2019, 9 pages (ISRG07810/PCT).
International Search Report and Written Opinion for Application No. PCT/US2017/061136, mailed on Feb. 19, 2018, 12 pages (ISRG07810/PCT).
Office Action for Chinese Application No. 201780073370, mailed Sep. 5, 2022, 31 pages.
Office Action for Korean Application No. KR20197016223, mailed May 24, 2022, 6 pages.
Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

TELEOPERATED SURGICAL SYSTEM WITH SURGEON SKILL LEVEL BASED INSTRUMENT CONTROL

CLAIM OF PRIORITY

This application is a continuation of U.S. application Ser. No. 16/349,202, filed May 10, 2019, which is a U.S. National Stage filing under 35 U.S.C. 371 from International Application PCT/US2017/061136, filed Nov. 10, 2017, which claims the benefit of priority to U.S. Patent application 62/421,072, filed on Nov. 11, 2016, each of which is incorporated by reference herein in its entirety.

BACKGROUND

1. Field of Invention

Inventive aspects are associated with medical devices used during surgery. More specifically, aspects are associated with surgical instrument use in accordance with surgeon skill level.

2. Art

Surgeons typically undertake extensive study before performing a surgical procedure. Traditionally, surgeons were limited to the study of generic anatomical models, such as photographs or drawings. More recently, various pre-operative diagnostic procedures (e.g., x-ray, CT, MRI, etc.) have made patient-specific anatomical information available.

In some cases, it is desirable to make additional, relevant anatomic and surgical procedure information available to a surgeon. In one aspect, it is desirable to provide a surgeon planning an operation on a particular patient with a surgical site video recording of an earlier surgical procedure performed on the particular patient. In another aspect, it is desirable to provide a surgeon with one or more surgical video recordings of surgical procedures on other patients that are similar to the surgical procedure planned for a particular patient. In one aspect, it is desirable to provide such information to a surgeon prior to the surgeon undertaking a particular surgical procedure. And in another aspect, it may be desirable to provide this information to a surgeon intraoperatively.

In one aspect, it is desirable to configure a video database that includes intraoperative surgical site video recordings of various procedures undergone by various patients. In one aspect, it is desirable to configure a medical device capable of video recording to further include an input that enables a surgeon using the medical device to highlight and annotate the video recording in real time as it is being recorded. In one aspect, it is desirable to configure a computer-based pattern matching algorithm to search through the individual records of the video database, identify relevant video records, and provide a surgeon with this relevant information for a particular surgical procedure.

SUMMARY

The following summary introduces certain aspects of the inventive subject matter in order to provide a basic understanding. This summary is not an extensive overview of the inventive subject matter, and it is not intended to identify key or critical elements or to delineate the scope of the inventive subject matter. Although this summary contains information that is relevant to various aspects and embodiments of the inventive subject matter, its sole purpose is to present some aspects and embodiments in a general form as a prelude to the more detailed description below.

A surgical method is provided for use with a teleoperated surgical system that includes a robotic surgical instrument. An image capture device is orientable toward a surgical site for capturing images of anatomical tissue and of robotic surgical instrument. A user display is coupled to the image capture device to show to a user, the captured images of the anatomical tissue and of the robotic surgical instrument. A user input command device is coupled to receive user input commands to control movement of the robotic surgical instrument. A movement controller circuit is coupled to receive the user input commands from the input command device. The movement controller circuit is configured to control movement of the robotic surgical instrument in response to the user input commands. The movement controller circuit is further configured to scale a rate of movement of the robotic surgical instrument, based at least in part upon a surgical skill level at using the robotic surgical instrument of the user providing the received user input commands, from a rate of movement indicated by the user input commands received at the user input command device.

A method is provided to operate a teleoperated surgical system that includes a robotic surgical instrument manipulator. User input commands are received from a user to control movement of a robotic surgical instrument mounted at the robotic surgical instrument manipulator. An identification determination is made of a robotic surgical instrument mounted at the robotic surgical instrument manipulator during the receiving the user input commands. A rate of movement of the robotic surgical instrument is scaled, based at least in part upon a skill level of the user at use of the identified surgical instrument, from a rate of movement indicated by the user input commands.

DETAILED DESCRIPTION

Figure 1:
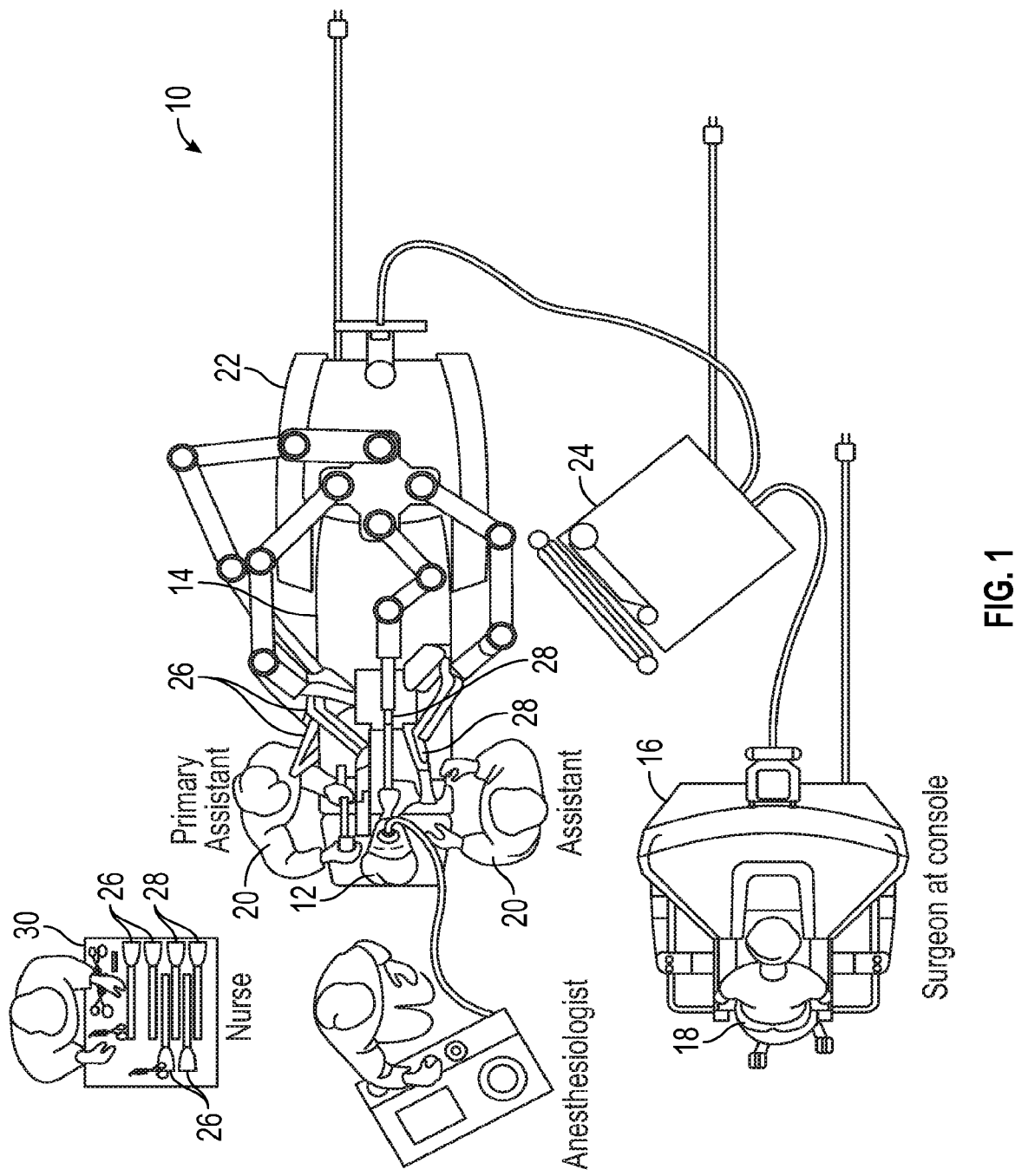
FIG. 1 is a plan view of a minimally invasive teleoperated surgical system.

This description and the accompanying drawings that illustrate inventive aspects, embodiments, implementations, or applications should not be taken as limiting—the claims define the protected invention. Various mechanical, compositional, structural, electrical, and operational changes may be made without departing from the scope of this description and the claims. In some instances, well-known circuits, structures, or techniques have not been shown or described in detail in order not to obscure the invention. Like numbers in two or more figures represent the same or similar elements.

Elements described in detail with reference to one embodiment, implementation, or application may, whenever practical, be included in other embodiments, implementations, or applications in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

Aspects of the invention are described primarily in terms of an implementation using a da Vinci® Surgical System (specifically, a Model IS4000, marketed as the da Vinci® Xi™ ID™ Surgical System), commercialized by Intuitive Surgical, Inc. of Sunnyvale, California. Knowledgeable persons will understand, however, that inventive aspects disclosed herein may be embodied and implemented in various ways, including robotic and, if applicable, non-robotic embodiments and implementations. Implementations on da Vinci® Surgical Systems (e.g., the Model IS4000 da Vinci® Xi™ Surgical System, the Model IS3000 da Vinci Si® Surgical System) are merely exemplary and are not to be considered as limiting the scope of the inventive aspects disclosed herein.

In accordance with various aspects, the present disclosure describes a surgical planning tool that includes a medical device configured to video record the performance of surgical procedures. The video recordings can be embedded with various metadata, e.g., highlights made by a medical person. Additionally, the video recordings can be tagged with various metadata, e.g., text annotations describing certain subject matter of the video, the identity of the patient to whom the video recording corresponds, biographical or medical information about the patient, and the like. In one aspect, tagged metadata is embedded in the video recordings.

In accordance with further aspects, the present disclosure describes a teleoperated medical device that includes a surgical instrument used to perform at least one surgical activity during a surgical procedure. Different stages of a surgical activities may require different surgical skill levels. In some embodiments, a surgical level in a surgical activity may be determined based at least in part upon a comparison of the surgeon's performance level of the surgical activity with the performance levels of other surgeons in the activity. A surgery may involve use of different surgical instruments during different portions of a surgical procedure. Each surgical instrument used during a surgery is controlled by one or more surgical instrument actuators operable in multiple actuator states. Which surgical instrument is in use during different portions of a surgery is tracked. In some embodiments, an actuator state of an actuator controlling a surgical instrument that is in use is tracked during surgical procedures. In some embodiments, surgeon eye movement also is tracked using a camera to determine direction of surgeon gaze during the surgery. In some embodiments, an information structure in a computer readable storage device associates surgical instrument in use and surgical instrument actuator states with surgical guidance information for presentation to a surgeon in response to a surgical instrument's use to perform the at least one surgical activity. In some embodiments, the surgical guidance information that is presented to a surgeon is determined based at least in part upon the surgeon's surgical skill level. In some embodiments, an information structure in a computer readable storage device associates at least one of a surgical instrument use during surgery or its specific actuator states during the performance of the at least one surgical activity with safety transition information for use to cause the surgical instrument actuator to transition to an actuator safety state of operation that matches a surgeon's skill level. In some embodiments, the surgical instrument actuator safety state of operation is determined based at least in part upon a surgeon's skill level.

In a teleoperated surgical system, different instruments may be used at different stages of a surgical procedure. Moreover, the same instrument may be used in different actuator states at different stages of a surgical procedure. As used herein, the term actuator state refers to a mechanical disposition of a surgical instrument as determined by an actuator, such as a motor, in response to input commands received from a surgeon or other surgical team member.

The video recordings and information structures that associate surgical instrument's use or specific actuator states with surgical guidance or actuator safety state information can be archived on an electronic medical record database implemented locally or on a cloud data storage service. The video recordings can be made available to interested health care providers. The information structures can be made available for use with the teleoperated medical device to provide surgical guidance and to control surgical instrument actuator state during performance of at least one surgical activity during performance of a surgical procedure.

Health care providers can search the medical device database based upon surgeon skill level for videos and information structure relationships of interest using the metadata tags described above. Additionally, in one aspect, the surgical planning tool includes a computer-based pattern matching and analysis algorithm. In one aspect, the pattern-matching algorithm culls through the videos stored on the electronic medical record database to identify correlations between visual characteristics in the video recordings and associated metadata tags made by medical persons. The surgical planning tool can apply these correlations to newly encountered anatomy, and thereby assist medical persons performing a procedure in making determinations about patient anatomy, preferred surgical approaches, disease states, potential complications, etc. In another aspect, the pattern matching algorithm culls through videos stored on the electronic medical record database to identify correlations between visual characteristics in the video recordings and patient health record information to identify patient anatomical characteristics that correlate with surgeon skill level information. The surgical planning tool can apply these correlations between anatomy and surgeon skill level records to a current patient's anatomy and health records, and thereby assist medical persons planning and performing a surgical procedure involving the current patient.

Minimally Invasive Teleoperated Surgical System

Referring now to the drawings, in which like reference numerals represent like parts throughout the several views, FIG. 1 is a plan view of a minimally invasive teleoperated surgical system 10, typically used for performing a minimally invasive diagnostic or surgical procedure on a patient 12 who is lying on an operating table 14. The system includes a surgeon's console 16 for use by a surgeon 18 during the procedure. One or more assistants 20 may also participate in the procedure. The minimally invasive teleoperated surgical system 10 further includes a patient-side cart 22 and an electronics cart 24. The patient-side cart 22 can manipulate at least one removably coupled surgical instrument 26 through a minimally invasive incision in the body of the patient 12 while the surgeon 18 views the surgical site through a user display within the surgeon's console 16. An image of the surgical site can be obtained by an image capture device such as a stereoscopic endoscope 28, which can be manipulated by the patient-side cart 22 to orient the endoscope 28 so as to capture images of patient anatomical structures and one or more surgical instruments at a surgical site. Computer processors located on the electronics cart 24 can be used to process the images of the surgical site for subsequent display to the surgeon 18 through a stereoscopic display at the surgeon's console 16. The number of surgical instruments 26 used at one time will generally depend on the diagnostic or surgical procedure and the space constraints within the operating room among other factors. If it is generally necessary to change one or more of the surgical instruments 26 being used during a procedure, an assistant 20 can remove the surgical instrument 26 from the patient-side cart 22, and replace it with another surgical instrument 26 from a tray 30 in the operating room.

Figure 2:
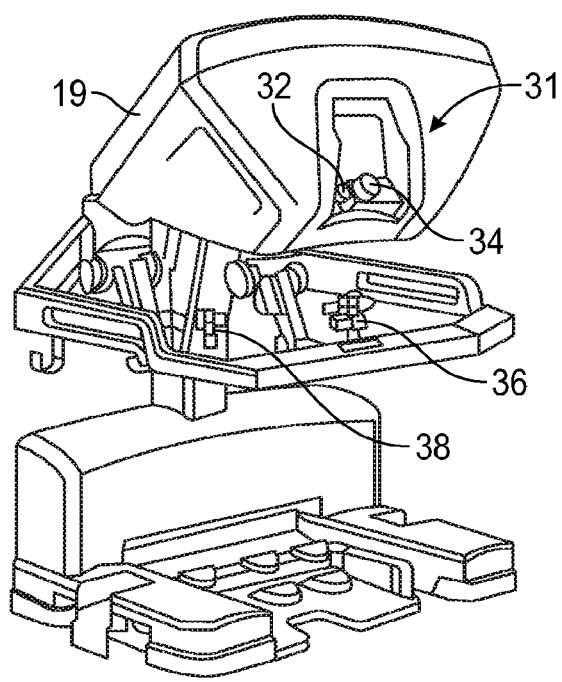
FIG. 2 is a perspective view of a surgeon's console.

FIG. 2 is a perspective view of the surgeon's console 16. The surgeon's console 16 includes a user display that includes a left eye display 32 and a right eye display 34 for presenting the surgeon 18 with a coordinated stereoscopic view of the surgical site that enables depth perception. The console 16 further includes an input command device that includes one or more manual control inputs that include hand grips 36, 38. One or more surgical instruments installed for use on the patient-side cart 22 (shown in FIG. 1) move in response to surgeon 18's manipulation of the one or more control inputs 36, 38. The control inputs 36, 38 can provide the same mechanical degrees of freedom as their associated surgical instruments 26 (shown in FIG. 1) to provide the surgeon 18 with telepresence, or the perception that the control inputs 36, 38 are integral with the instruments 26 so that the surgeon has a strong sense of directly controlling the instruments 26. To this end, position, force, and tactile feedback sensors (not shown) may be employed to transmit position, force, and tactile sensations from the surgical instruments 26 back to the surgeon's hands through the control inputs 36, 38.

The surgeon's console 16 is usually located in the same room as the patient so that the surgeon can directly monitor the procedure, be physically present if necessary, and speak to a patient-side assistant directly rather than over the telephone or other communication medium. But, the surgeon can be located in a different room, a completely different building, or other remote location from the patient allowing for remote surgical procedures.

Figure 3:
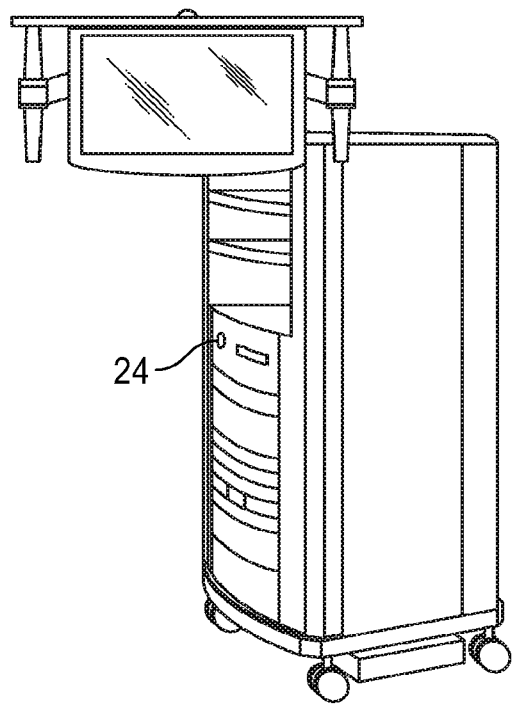
FIG. 3 is a perspective view of an electronics cart.

FIG. 3 is a perspective view of the electronics cart 24. The electronics cart 24 can be coupled with the endoscope 28 and includes a computer processor to process captured images for subsequent display, such as to a surgeon on the surgeon's console 16, or on another suitable display located locally and/or remotely. For example, if a stereoscopic endoscope is used, a computer processor on electronics cart 24 can process the captured images to present to the surgeon at the left and right eye displays 32, 34, coordinated stereo images of the surgical site. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations. Optionally, equipment in electronics cart may be integrated into the surgeon's console or the patient-side cart, or it may be distributed in various other locations in the operating room.

Figure 4:
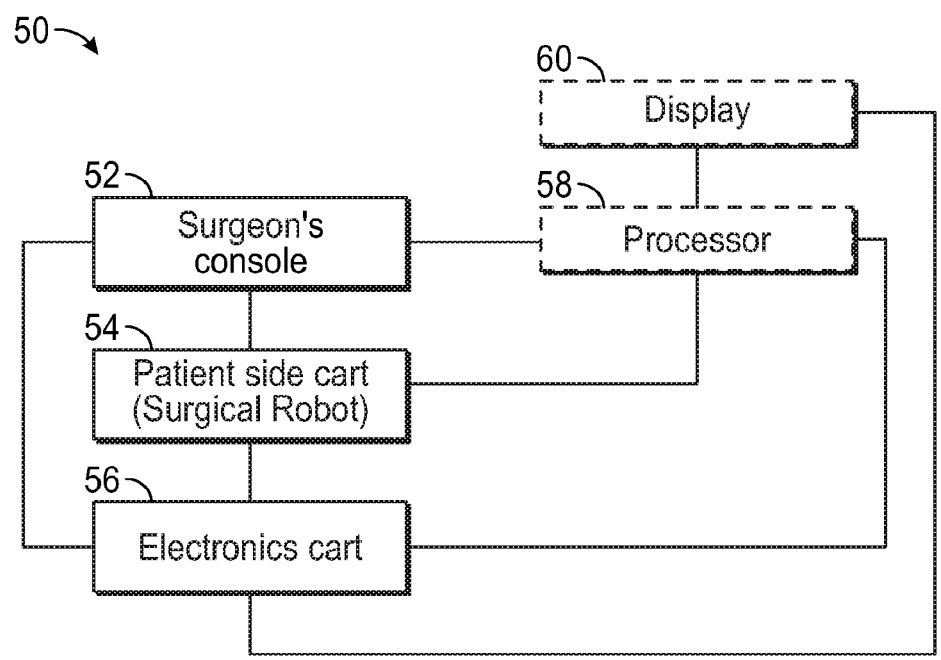
FIG. 4 is a diagrammatic illustration of a teleoperated surgical system.

FIG. 4 diagrammatically illustrates a teleoperated surgical system 50 (such as the minimally invasive teleoperated surgical system 10 of FIG. 1). A surgeon's console 52 (such as surgeon's console 16 in FIG. 1) can be used by a surgeon to control a patient-side cart 54 (such as patent-side cart 22 in FIG. 1) during a minimally invasive procedure. The patient-side cart 54 can use an imaging device, such as a stereoscopic endoscope, to capture images of a surgical site and output the captured images to a computer processor located on an electronics cart 56 (such as the electronics cart 24 in FIG. 1). The computer processor typically includes one or more data processing boards purposed for executing computer readable code stored in a non-volatile memory device of the computer processor. In one aspect, the computer processor can process the captured images in a variety of ways prior to any subsequent display. For example, the computer processor can overlay the captured images with a virtual control interface prior to displaying the combined images to the surgeon via the surgeon's console 52.

Additionally, or in the alternative, the captured images can undergo image processing by a computer processor located outside of electronics cart 56. In one aspect, teleoperated surgical system 50 includes an optional computer processor 58 (as indicated by dashed line), which includes one or more central processing units (CPUs) similar to the computer processor located on electronics cart 56, and patient-side cart 54 outputs the captured images to computer processor 58 for image processing prior to display on the surgeon's console 52. In another aspect, captured images first undergo image processing by the computer processor on electronics cart 56 and then undergo additional image processing by computer processor 58 prior to display on the surgeon's console 52. Teleoperated surgical system 50 can include an optional display 60, as indicated by dashed line. Display 60 is coupled with the computer processor located on the electronics cart 56 and with computer processor 58, and captured images processed by these computer processors can be displayed on display 60 in addition to being displayed on a display of the surgeon's console 52.

Moreover, the control inputs 36, 38 are coupled to receive user input commands to control movement of one or more surgical instruments at the surgical site. The processor 58 acts as a kinematic movement controller circuit that is coupled to receive the user input commands from the control inputs 36, 38. The processor 58 translates user input in the form of physical movement of the control inputs 36, 38 to control signals to control motors to control corresponding movement of one or more surgical instruments to a movement controller within the patient side cart 54 to impart corresponding movement to an endoscope or to one or more surgical instruments. The translation of user input movement imparted by a user's hand motions upon control inputs 36, 38 to corresponding instrument movement imparted by motors coupled to the surgical instruments involves kinematic movement translation, which typically involves scaling of distances such that an instrument may be moved by only a small fraction of the distance that a control inputs 36 or 38 is moved to impart a user command to cause the instrument movement. In other words, user input movement imparted to control inputs 36, 38 in user space is translated to corresponding smaller scale movements in instrument space at the surgical site. An example of kinematic movement translation in a teleoperated surgical system is described in U.S. Pat. No. 6,424,885.

Figure 5:
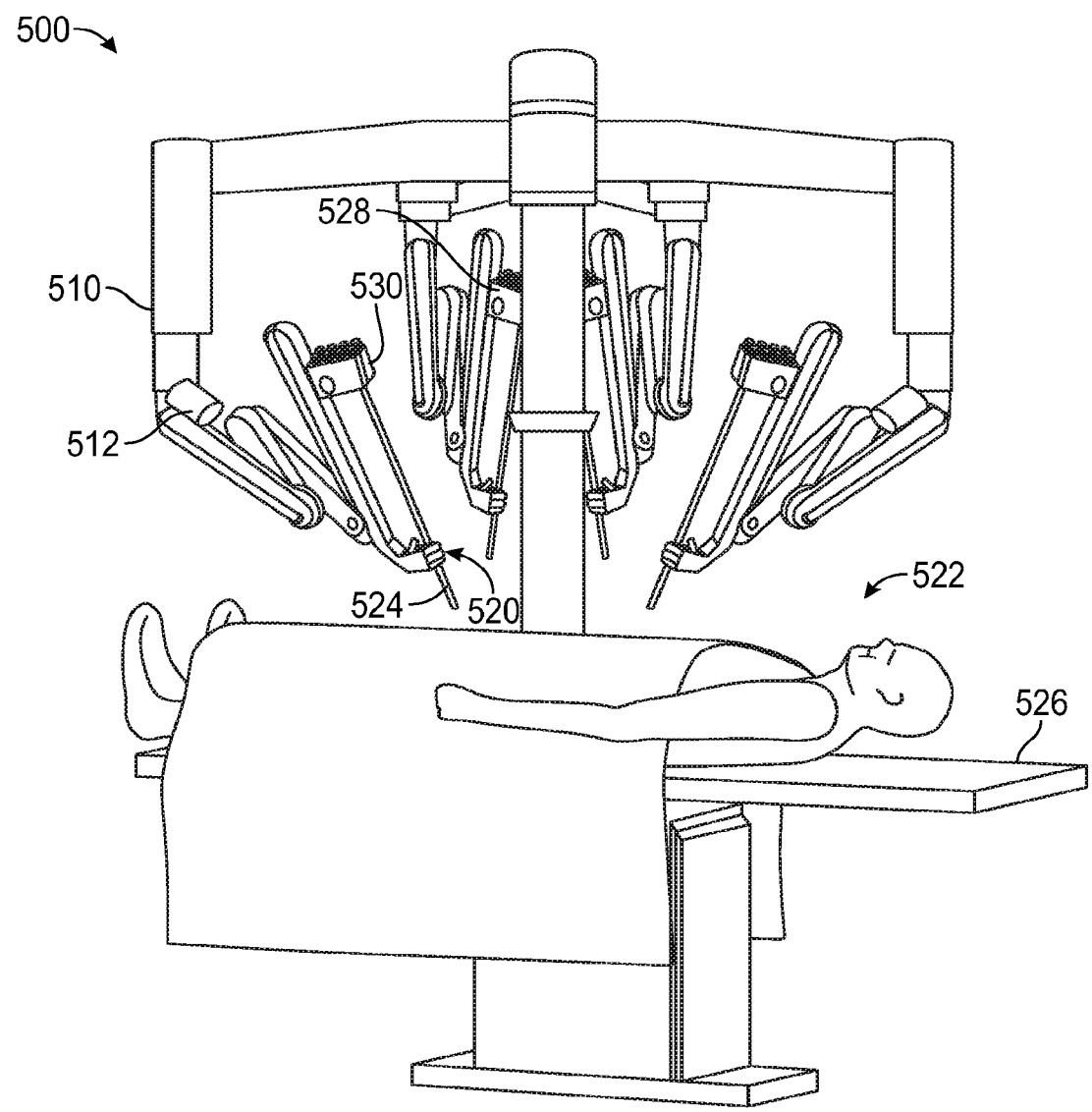
FIG. 5 is a perspective view of a patient-side cart.

FIG. 5 is a perspective view of a patient-side cart 500 of a minimally invasive teleoperated surgical system, in accordance with embodiments of the present invention. The patient-side cart 500 includes one or more support assemblies 510. A surgical instrument manipulator 512 is mounted at the end of each support assembly 510. Additionally, each support assembly 510 can optionally include one or more unpowered, lockable setup joints that are used to position the attached surgical instrument manipulator 512 with reference to the patient for surgery. As depicted, the patient-side cart 500 rests on the floor. In other embodiments, operative portions of the patient-side cart can be mounted to a wall, to the ceiling, to the operating table 526 that also supports the patient's body 522, or to other operating room equipment. Further, while the patient-side cart 500 is shown as including four surgical instrument manipulators 512, more or fewer surgical instrument manipulators 512 may be used.

A functional minimally invasive teleoperated surgical system will generally include a vision system portion that enables a user of the teleoperated surgical system to view the surgical site from outside the patient's body 522. The vision system typically includes a camera instrument 528 for capturing video images and one or more video displays for displaying the captured video images. In some surgical system configurations, the camera instrument 528 includes optics that transfer the images from a distal end of the camera instrument 528 to one or more imaging sensors (e.g., CCD or CMOS sensors) outside of the patient's body 522. Alternatively, the imaging sensor(s) can be positioned at the distal end of the camera instrument 528, and the signals produced by the sensor(s) can be transmitted along a lead or wirelessly for processing and display on the one or more video displays. One example of a video display is the stereoscopic display on the surgeon's console in surgical systems commercialized by Intuitive Surgical, Inc., Sunnyvale, California.

Referring to FIG. 5, mounted to each surgical instrument manipulator 512 is a surgical instrument 520 that operates at a surgical site within the patient's body 522. Each surgical instrument manipulator 512 can be provided in a variety of forms that allow the associated surgical instrument to move with one or more mechanical degrees of freedom (e.g., all six Cartesian degrees of freedom, five or fewer Cartesian degrees of freedom, etc.). Typically, mechanical or control constraints restrict each manipulator 512 to move its associated surgical instrument around a center of motion on the instrument that stays stationary with reference to the patient, and this center of motion is typically located at the position where the instrument enters the body.

In one aspect, surgical instruments 520 are controlled through computer-assisted teleoperation. A functional minimally invasive teleoperated surgical system includes a control input that receives inputs from a user of the teleoperated surgical system (e.g., a surgeon or other medical person). The control input is in communication with one or more computer-controlled teleoperated actuators, such as one or more motors to which surgical instrument 520 is coupled. In this manner, the surgical instrument 520 moves in response to a medical person's movements of the control input. In one aspect, one or more control inputs are included in a surgeon's console such as surgeon's console 16 shown at FIG. 2. A surgeon can manipulate control inputs 36 of surgeon's console 16 to operate teleoperated actuators of patient-side cart 500. The forces generated by the teleoperated actuators are transferred via drivetrain mechanisms, which transmit the forces from the teleoperated actuators to the surgical instrument 520.

Referring to FIG. 5, in one aspect, a surgical instrument 520 and a cannula 524 are removably coupled to manipulator 512, with the surgical instrument 520 inserted through the cannula 524. One or more teleoperated actuators of the manipulator 512 move the surgical instrument 512 as a whole. The manipulator 512 further includes an instrument carriage 530. The surgical instrument 520 is detachably connected to the instrument carriage 530. In one aspect, the instrument carriage 530 houses one or more teleoperated actuators inside that provide a number of controller motions that the surgical instrument 520 translates into a variety of movements of an end effector on the surgical instrument 520. Thus the teleoperated actuators in the instrument carriage 530 move only one or more components of the surgical instrument 520 rather than the instrument as a whole. Inputs to control either the instrument as a whole or the instrument's components are such that the input provided by a surgeon or other medical person to the control input (a "master" command) is translated into a corresponding action by the surgical instrument (a "slave" response).

In an alternate embodiment, instrument carriage 530 does not house teleoperated actuators. Teleoperated actuators that enable the variety of movements of the end effector of the surgical instrument 520 are housed in a location remote from the instrument carriage 530, e.g., elsewhere on patient-side cart 500. A cable-based force transmission mechanism or the like is used to transfer the motions of each of the remotely located teleoperated actuators to a corresponding instrument-interfacing actuator output located on instrument carriage 530. In some embodiments, the surgical instrument 520 is mechanically coupled to a first actuator, which controls a first motion of the surgical instrument such as longitudinal (z-axis) rotation. The surgical instrument 520 is mechanically coupled to a second actuator, which controls second motion of the surgical instrument such as two-dimensional (x, y) motion. The surgical instrument 520 is mechanically coupled to a third actuator, which controls third motion of the surgical instrument such as opening and closing or a jaws end effector.

Figure 6:
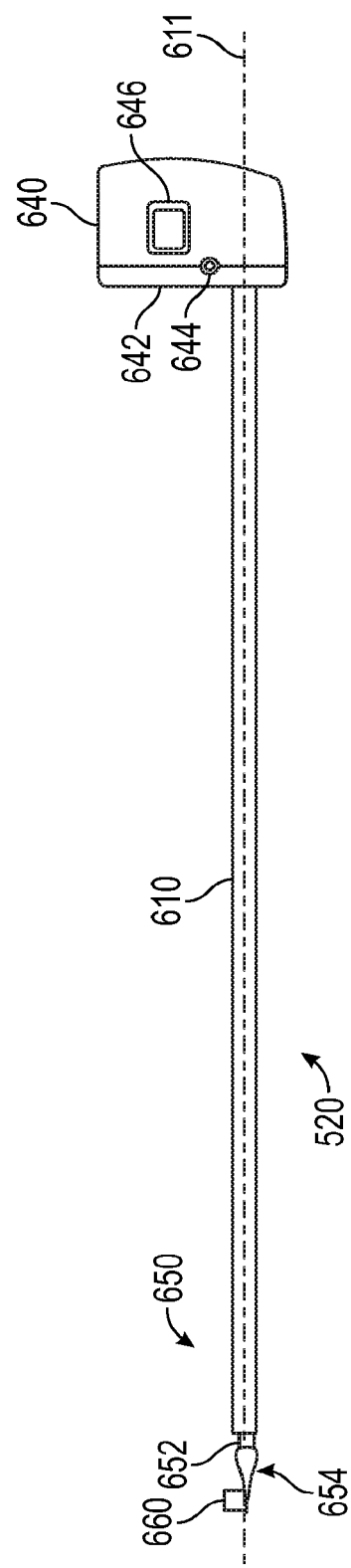
FIG. 6 is an elevation view of a surgical instrument.

FIG. 6 is a side view of a surgical instrument 520, which includes a distal portion 650 and a proximal control mechanism 640 coupled by an elongate tube 610 having an elongate tube centerline axis 611. The surgical instrument 520 is configured to be inserted into a patient's body and is used to carry out surgical or diagnostic procedures. The distal portion 650 of the surgical instrument 520 can provide any of a variety of end effectors 654, such as the forceps shown, a needle driver, a cautery device, a cutting tool, an imaging device (e.g., an endoscope or ultrasound probe), or the like. The surgical end effector 654 can include a functional mechanical degree of freedom, such as jaws that open or close, or a knife that translates along a path. In the embodiment shown, the end effector 654 is coupled to the elongate tube 610 by a wrist 652 that allows the end effector to be oriented relative to the elongate tube centerline axis 611. Surgical instrument 520 can also contain stored (e.g., on a semiconductor memory inside the instrument) information, which may be permanent or may be updatable by a surgical system configured to operate the surgical instrument 520. Accordingly, the surgical system may provide for either one-way or two-way information communication between the surgical instrument 520 and one or more components of the surgical system.

Figure 7:
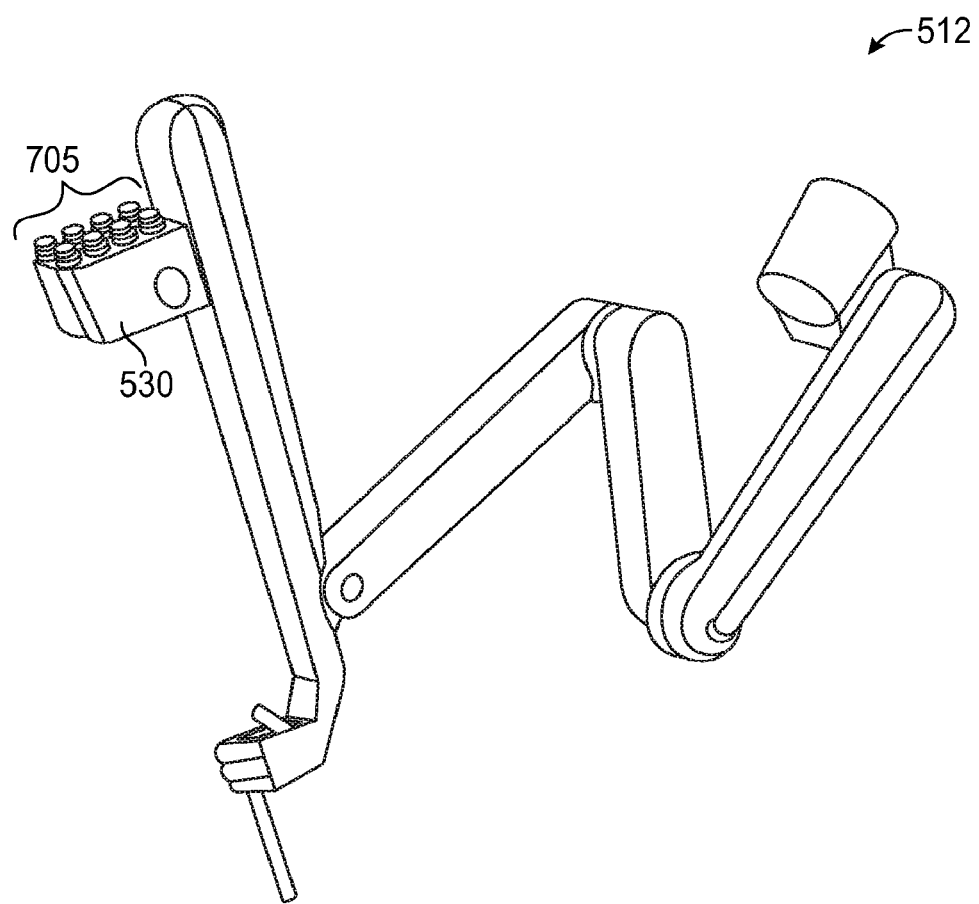
FIG. 7 is a perspective view of an instrument manipulator.

FIG. 7 is a perspective view of surgical instrument manipulator 512. Instrument manipulator 512 is shown with no surgical instrument installed. Instrument manipulator 512 includes an instrument carriage 530 to which a surgical instrument (e.g., surgical instrument 520) can be detachably connected. Instrument carriage 530 houses a plurality of teleoperated actuators. Each teleoperated actuator includes an actuator output 705. When a surgical instrument is installed onto instrument manipulator 512, one or more instrument inputs (not shown) of an instrument proximal control mechanism (e.g., proximal control mechanism 640 at FIG. 6) are mechanically coupled with corresponding actuator outputs 705. In one aspect, this mechanical coupling is direct, with actuator outputs 705 directly contacting corresponding instrument inputs. In another aspect, this mechanical coupling occurs through an intermediate interface, such as a component of a drape configured to provide a sterile barrier between the instrument manipulator 512 an associated surgical instrument.

In one aspect, movement of one or more instrument inputs by corresponding teleoperated actuators results in a movement of a surgical instrument mechanical degree of freedom. For example, in one aspect, the surgical instrument installed on instrument manipulator 512 is surgical instrument 520, shown at FIG. 6. Referring to FIG. 6, in one aspect, movement of one or more instrument inputs of proximal control mechanism 640 by corresponding teleoperated actuators rotates elongate tube 610 (and the attached wrist 652 and end effector 654) relative to the proximal control mechanism 640 about elongate tube centerline axis 611. In another aspect, movement of one or more instrument inputs by corresponding teleoperated actuators results in a movement of wrist 652, orienting the end effector 654 relative to the elongate tube centerline axis 611. In another aspect, movement of one or more instrument inputs by corresponding teleoperated actuators results in a movement of one or more moveable elements of the end effector 654 (e.g., a jaw member, a knife member, etc.). Accordingly, various mechanical degrees of freedom of a surgical instrument installed onto an instrument manipulator 512 can be moved by operation of the teleoperated actuators of instrument carriage 530.

Annotating a Recorded Video

Figure 8:
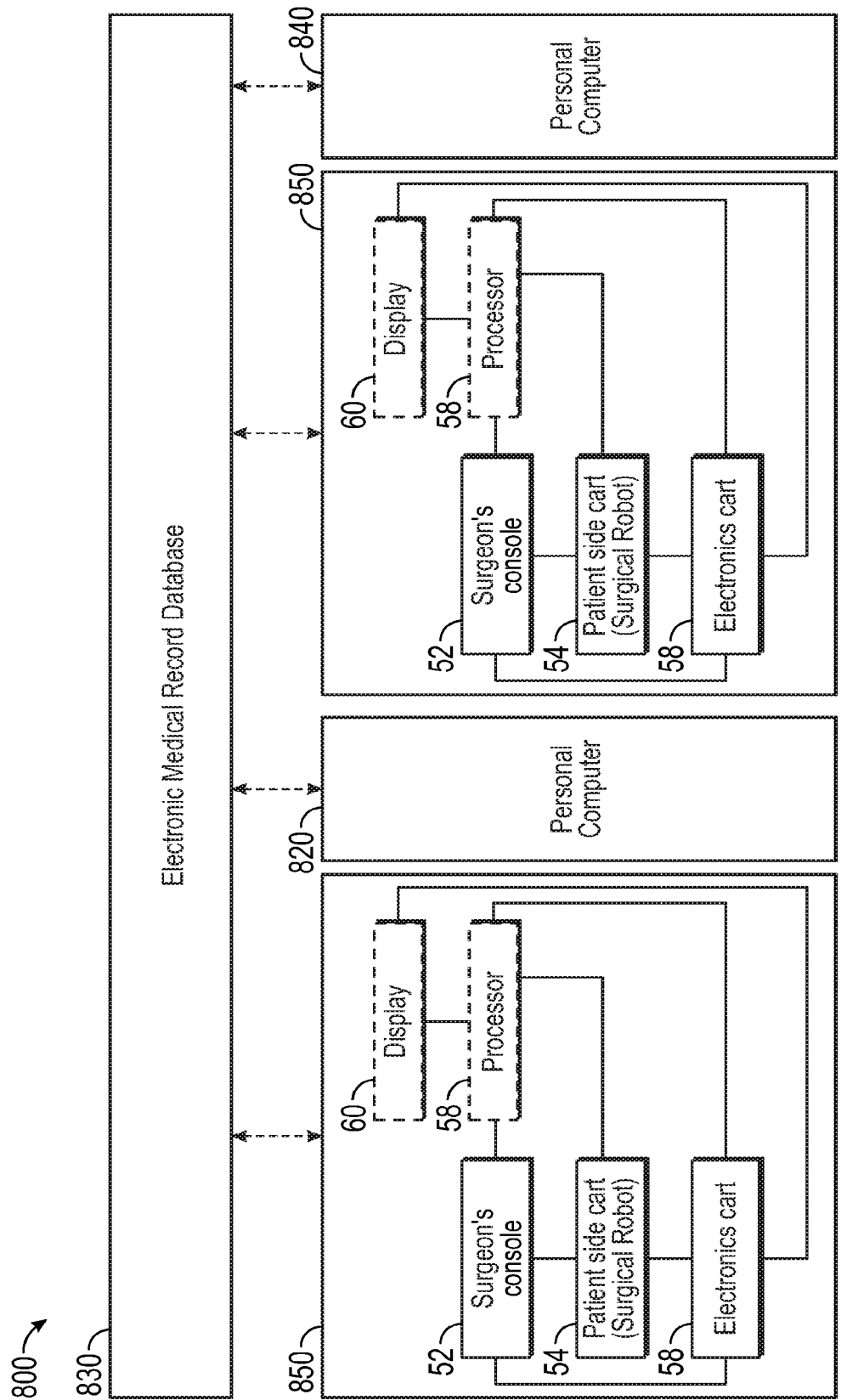
FIG. 8 is a diagrammatic illustration of a surgical planning tool.

FIG. 8 shows a schematic diagram of an exemplary surgical planning tool 800. In one aspect, surgical planning tool 800 includes a teleoperated surgical system 850 in data communication with an electronic medical device record database 830. Teleoperated surgical system 850 shown here is similar to teleoperated surgical system 850 shown at FIG. 4. In one aspect, electronic medical record database 830 includes the medical records of patients that have undergone treatment at a particular hospital. Database 830 can be implemented on a server located on-site at the hospital. The medical record entries contained in the database 830 can be accessed from hospital computers through an intranet network. Alternatively, database 830 can be implemented on a remote server located off-site from the hospital, e.g., using one of a number of cloud data storage services. In this case, medical record entries of database 830 are stored on the cloud server, and can be accessed by a computer with internet access.

In one aspect, a surgical procedure is performed on a first patient using teleoperated surgical system 850. An imaging device associated with teleoperated surgical system 850 captures images of the surgical site and displays the captured images as frames of a video on a display of surgeon's console 52. In one aspect, a medical person at surgeon's console 52 highlights or annotates certain patient anatomy shown in the displayed video using an input device of surgeon's console 52. An example of such an input device is control input 36 shown at FIG. 2, which is coupled to a cursor that operates in conjunction with a graphic user interface overlaid onto the displayed video. The graphic user interface can include a QWERTY keyboard, a pointing device such as a mouse and an interactive screen display, a touch-screen display, or other means for data or text entry. Accordingly, the medical person can highlight certain tissue of interest in the displayed image or enter a text annotation.

In one aspect, the surgical site video is additionally displayed on a display located on electronics cart 56. In one aspect, the display of electronics cart is a touch-screen user interface usable by a medical person to highlight and annotate certain portions of patient anatomy shown on an image that is displayed for viewing on the display on the electronics cart. A user, by touching portions of patient anatomy displayed on the touch-screen user interface, can highlight portions of the displayed image. Additionally, a graphic interface including a QWERTY keyboard can be overlaid on the displayed image. A user can use the QWERTY keyboard to enter text annotations.

In one aspect, the surgical site video captured by the imaging device associated with teleoperated surgical system 850 is recorded by the teleoperated surgical system 850, and stored on database 830, in addition to being displayed in real time or near real time to a user. Highlights and/or annotations associated with the recorded video that were made by the user can also be stored on database 830. In one aspect, the highlights made by the user are embedded with the recorded video prior to its storage on database 830. At a later time, the recorded video can be retrieved for viewing. In one aspect, a viewer of the recorded video can select whether the highlights are displayed or suppressed from view. Similarly, annotations associated with the recorded video can also be stored on database 830. In one aspect, the annotations made by the user are used to tag the recorded video, and can be used to provide as a means of identifying the subject matter contained in the recorded video. For example, one annotation may describe conditions of a certain disease state. This annotation is used to tag the recorded video. At a later time, a person desiring to view recorded procedures concerning this disease state can locate the video using a key word search.

Retrieval of Stored Video

In some cases, it is desirable for a medical person to be able to view video recordings of past surgical procedures performed on a given patient. In one aspect, a patient who previously underwent a first surgical procedure to treat a medical condition subsequently requires a second surgical procedure to treat recurrence of the same medical condition or to treat anatomy located nearby to the surgical site of the first surgical procedure. In one aspect, the surgical site events of the first surgical procedure were captured in a surgical site video recording, and the video recording was archived in database 830 as part of the patient's electronic medical records. Prior to performing the second surgical procedure on the patient, a medical person can perform a search of database 830 to locate the video recording of the patient's earlier surgical procedure.

In some cases, it is desirable for a medical person planning to perform a surgical procedure on a patient to be able to view video recordings of similar surgical procedures performed on persons having certain characteristics similar to the patient. In one aspect, surgical site video recordings of surgical procedures can be tagged with metadata information such as the patient's age, gender, body mass index, genetic information, type of procedure the patient underwent, etc., before each video recording is archived in database 830. In one aspect, the metadata information used to tag a video recording is automatically retrieved from a patient's then-existing medical records, and then used to tag the video recording before the video recording is archived in database 830. Accordingly, prior to performing a medical procedure on a patient, a medical person can search database 830 for video recordings of similar procedures performed on patients sharing certain characteristics in common with the patient. For example, if the medical person is planning to use teleoperated surgical system 850 to perform a prostatectomy on a 65-year-old male patient with an elevated body mass index using, the medical person can search database 830 for surgical site video recordings of prostatectomies performed using teleoperated surgical system 850 on other males of similar age and having similarly elevated body mass index.

In one aspect, a video recording of a surgical procedure is communicated by database 830 to an optional personal computer 820 (as indicated by dashed line), and made available for viewing by a medical person who plans to perform a surgical procedure. Additionally, or in the alternative, the video recording of the earlier surgical procedure can be communicated by database 830 to teleoperated surgical system 850, and made available for viewing pre-operatively or intraoperatively. In one aspect, the video recording is displayed by teleoperated surgical system 850 on a display located on surgeon's console 52. In another aspect, the video recording of the first surgical procedure is displayed on a display located on electronics cart 56.

Cloud-Based Video Database

In one aspect, database 830 is implemented on a remote server using a cloud data storage service and is accessible by multiple health care providers. Referring to FIG. 8, as shown by dashed line, surgical planning tool 800 optionally includes teleoperated surgical system 850 (as indicated by dashed line) and personal computer 840 (as indicated by dashed line). In one aspect, teleoperated surgical system 850 is similar to teleoperated surgical system 850 and personal computer 840 is similar to personal computer 820, except that teleoperated surgical system 850 and personal computer 820 are located at a first health care provider and teleoperated surgical system 850 and personal computer 840 are located at a second health care provider. In one aspect, a first patient requires surgical treatment of a medical condition, and undergoes a surgical procedure using teleoperated surgical system 850 at the first health care provider. A video recording of the surgical procedure is archived on database 830. At a later time, a second patient requires surgical treatment of the same medical condition, and plans to receive surgical treatment using teleoperated surgical system 850 at the second health care provider. Prior to performing the surgical procedure on the second patient, a medical person accesses database 830 through a secure internet connection and searches database 830 for surgical site video recordings of similar procedures. In one aspect, the medical person treating the second patient is able to retrieve from database 830 the video recording of first patient's surgical procedure, without acquiring knowledge of the identity of the first patient. In this manner, the privacy of the first patient is maintained. In one aspect, the video recording of the first patient's surgical procedure includes highlights and/or annotations made by the medical person who treated the first patient.

Computer Based Pattern Matching and Analysis

Surgical planning tool 800 can includes a pattern matching and analysis algorithm implemented in the form of computer executable code. In one aspect, the pattern matching and analysis algorithm is stored in a non-volatile memory device of surgical planning tool 800, and is configured to analyze the video recordings archived in database 830. As discussed previously, each of the video recordings archived in database 830 can be tagged and/or embedded with certain metadata information. This metadata information can include patient information such as patient age, gender, and other information describing the patient's health or medical history. Additionally, as discussed previously, the metadata information can include highlights or annotations made by a medical person. In one aspect, these highlights and annotations are embedded with the video recording and archived together with the video in database 830.

In one aspect, pattern matching and analysis algorithm includes an image analysis component that identifies patterns in shapes and colors that are shared amongst multiple video recordings stored on database 830. The pattern matching and analysis algorithm then reviews the tagged metadata associated with this subset of video recordings to determine whether any words or phrases are frequently associated with videos within this subset. These analyses performed by pattern matching and analysis algorithm can be used to assist medical persons in making determinations about patient anatomy, preferred surgical approaches, disease states, potential complications, etc.

A Method of Using a Surgical Planning Tool

Figure 9:
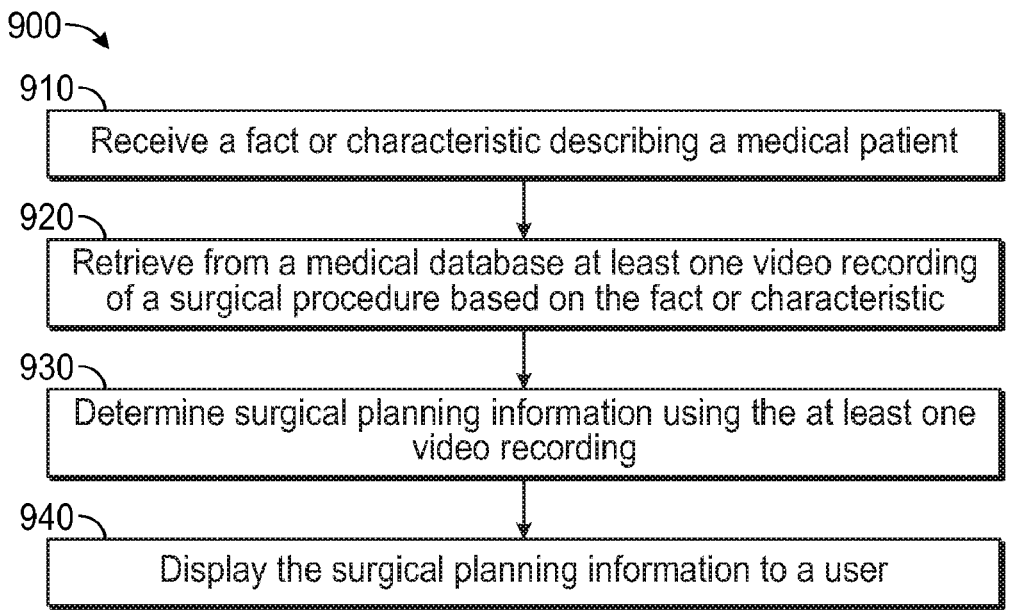
FIG. 9 is a flow diagram of a method of using a surgical planning tool.

FIG. 9 shows a method 900 of using a surgical planning tool. In one aspect, the surgical planning tool is similar to surgical planning tool 800 at FIG. 8. At 910, a fact or characteristic describing a medical patient, e.g., a medical condition suffered by a patient, is received by a medical device. Medical device can receive this fact or circumstance via a user interface located on a teleoperated surgical system (e.g., teleoperated surgical system 10 at FIG. 1 or teleoperated surgical system 50 at FIG. 4), or alternatively, through a personal computer similar to personal computer 820 at FIG. 2. At 920, the medical device uses the fact or characteristic received at 910 to retrieve at least one relevant video recording of a surgical procedure from a medical device database. At 930, the medical device uses the video recordings to determine surgical planning information. In one aspect, the surgical planning information includes the types of instruments used in the recorded procedure. At 940, the medical device displays to a user the surgical planning information determined at 930.

A Method of Using Surgical Skill Level to Guide a Surgical Procedure

Chart 1 identifies several example distinct core set of surgical instrument skills have been identified that are useful during a teleoperated surgical procedure in accordance with Assessment of Robotic Console Skills (ARCS) criteria.

CHART 1

Surgical Skill
Bimanual wrist manipulation
Camera Control
Master clutching to manage hand position
Use of a third instrument arm
Activating an energy source
Appropriate depth perception
Awareness of forces applied by instruments In some embodiments, surgical skill level for a category are rated as novice, intermediate and experienced. A surgeon's skill level may vary from one skill category to the next. The skill assessment scale is generally applicable to any multiport robotically assisted surgical procedure, regardless of surgical specialty.

Figure 10:
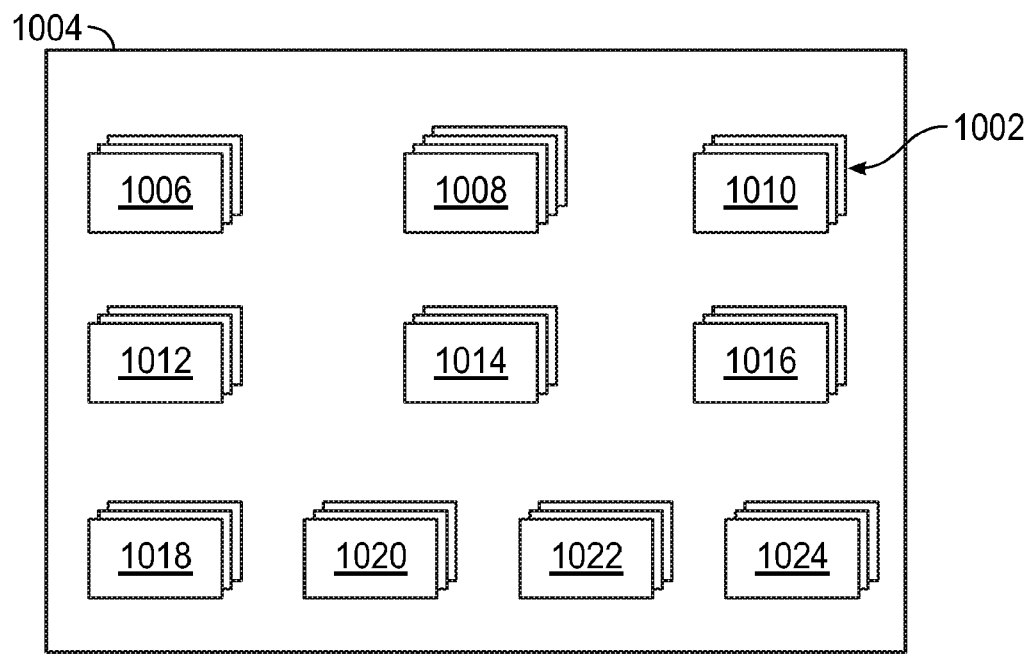
FIG. 10 is an illustrative drawing representing storage atlas in a computer readable storage device in accordance with some embodiments.

FIG. 10 is an illustrative drawing representing storage atlas in a computer readable storage device 1004 in accordance with some embodiments. The storage atlas 1002 includes first information structures 1006 that indicates instances of previously performed surgical procedures. A second information structures 1008 that indicates teleoperated surgical instrument actuation states during the previously performed surgical procedures. A third information structure 1010 associates a surgical procedure with surgical activities during the surgical procedure. A fourth information structures 1012 associates a surgeon with the surgeon's surgical skill levels. A fifth information structure 1014 associates surgical procedures with surgical instrument actuation states. A sixth information structure 1016 associates surgeon skill levels during different activates with different messages. A seventh information structure 1018 associates surgeon skill levels with during different activates with different surgical instrument safety actuation states. A ninth information structure 1019 associates recorded video information from individual surgeries with corresponding surgical instrument actuator state information and recorded surgeon eye movements during the surgeries in accordance with some embodiments.

In some embodiments, information in the various information structures 1004-1019 are evaluated to identify correlations between surgeon skill levels and surgical procedure results/risks. In some embodiments, information in the various information structures 1004-1019 are evaluated to identify correlations between patient safety concerns/risks and surgical activities during a surgical procedure. In some embodiments, teleoperated surgical procedures are evaluated to identify correlations between patient safety concerns/risks and surgical instrument actuator state during a surgical activity as a function of surgeon skill level. In some embodiments the storage atlas 1002 includes a tenth information structures 1020 to provide a correlation between surgical outcomes/risks and surgical instrument actuator state during a surgical activity as a function of surgeon skill level. These evaluations may involve machine learning (ML) techniques, for example.

The storage atlas 1002 includes data concerning surgeries on prior patients and the prior surgeons who performed the prior surgeries. In some embodiments, the storage atlas 1002 includes video images of surgical scenes from prior surgeries and corresponding annotations such as text and telestration tags 1022. In some embodiments, the storage atlas 1002 includes recordings 1024 of surgical instrument actuator states during the prior surgeons' performance of surgical activities in the prior surgeries.

Figure 11:
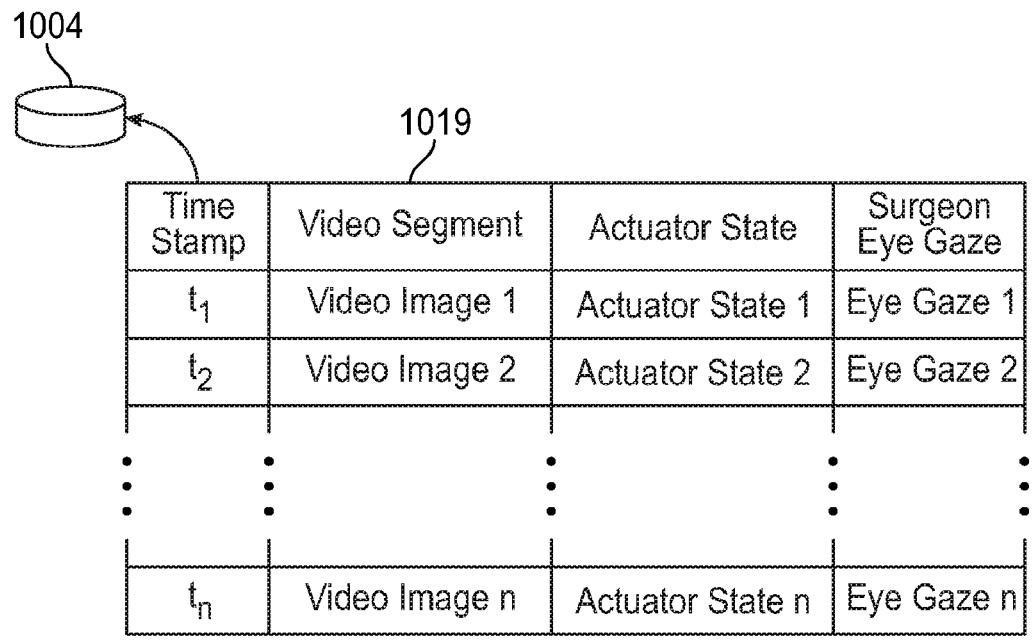
FIG. 11 is an illustrative drawing representing an example of the ninth information structure included within the atlas in the storage device, which associates recorded video information from an individual surgery with corresponding surgical instrument actuator state information and surgeon eye movement information in accordance with some embodiments.

FIG. 11 is an illustrative drawing representing an example of the seventh information structure 1018 included within the atlas 1002 in the storage device 1004, which associates recorded video information from an individual surgery with corresponding surgical instrument actuator state information in accordance with some embodiments. In one aspect, video recording images of patient anatomy during a surgery, surgical instrument actuator states during the surgery, and surgeon eye movement during the surgery are time stamped (t1, t2 . . . tn) so as to produce a chronological record of times of occurrence of surgical activities upon patient anatomy, to provide a corresponding chronological record of times of occurrence of surgical instrument actuator states and to provide a corresponding chronological record of surgical eye movement during a surgical procedure. Thus, time stamps recorded during a surgical procedure are used to temporally align video images anatomy, with surgical instrument actuator states and surgeon eye gaze.

During a surgery, a user may annotate the video recording and the surgical instrument actuation state recording with metadata that indicate corresponding surgical activity such as vessel sealing, suture knot-tying or blunt tissue dissection, for example. The annotation may include one or more of or a combination of written notes tagged to video information and/or surgical instrument actuation state information, coloring or highlighting (e.g., telestration) of images in the video recordings, for example. The annotations may be time stamped for use to temporally align them with corresponding video recording information and corresponding recorded surgical instrument state information.

During a teleoperated surgical procedure, a surgical activity such as neurovascular bundle dissection (nerve sparing), often involves use of multiple surgical instruments such as a prograsper and robotic scissors, each having its own actuator state. Thus, different surgical activities often require combinations of multiple surgical instrument skills. For example, performance of a continuous suturing surgical activity often requires the following combination of surgical skills: instrument wrist manipulation, needle grasping, needle passing and orientation between two instruments, tissue grasping, and needle driving.

Figures 12A, 12B, 12C:
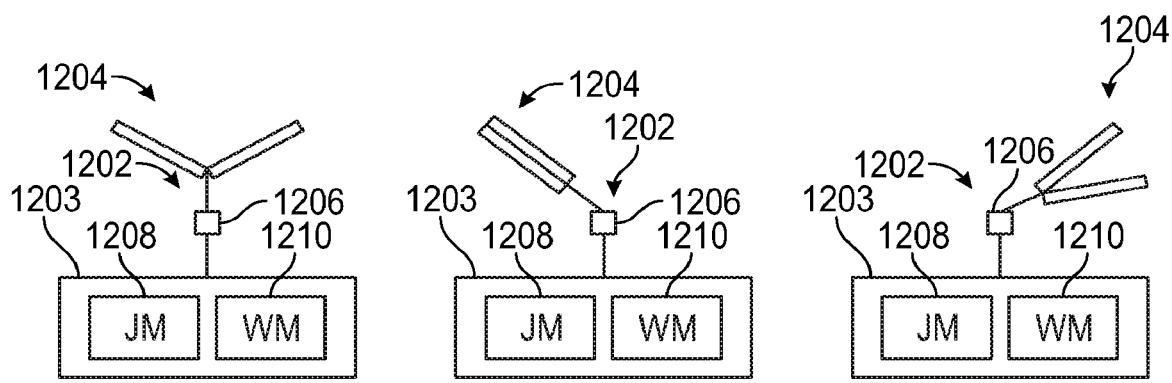
FIGS. 12A-12C are illustrative drawings showing an example surgical instrument and an actuator assembly in which the surgical instrument is shown in three different example operational states in accordance with some embodiments.

FIGS. 12A-12C are illustrative drawings showing an example surgical instrument 1202 and an actuator assembly 1203 in which the surgical instrument is shown in three different example operational states in accordance with some embodiments. The example instrument 1202 includes a jaw end effector 1204 that can transition between open and closed states and a continuum of partially opened/partially closed states in between. The example instrument 1202 also includes a two degree of freedom (2-dof) wrist 1206 that can move between different two-dimensional (x, y) positional states. The example actuator assembly 1203 includes a first actuator 1208, which in some embodiments includes a jaw motor (JM) used to actuate the jaw end effector 1204. The example actuator assembly 1203 includes a second actuator 1210, which in some embodiments includes a wrist motor (WM) used to actuate the wrist 1206. During a surgery, the surgical instrument 1202 may transition through multiple actuation states corresponding to different activities during a surgical procedure. As represented in FIG. 12A, for example, a surgical procedure may involve a first surgical activity in which the first actuator 1208 (the JM) disposes the jaw end effector 1204 to a fully open state and the second actuator 1210 the (WM) disposes the wrist 1206 to a first positional state (x1, y1). As represented in FIG. 12B, for example, the surgical procedure may involve a second surgical activity in which the first actuator 1208 transitions the jaw end effector 1204 to a fully closed state and the second actuator 1210 transitions the wrist 1206 to a second positional state (x2, y2). As represented in FIG. 12C, for example, the surgical procedure may involve a third surgical activity in which the first actuator 1208 disposes the jaw end effector 1104 in a partially open/partially closed state and the second actuator 1210 transitions the wrist 1206 to a third positional state (x3, y3).

In some embodiments, performance of a teleoperated surgical system in response to a surgeon's input control commands is scaled based upon the surgeon's skill level for surgical activities performed using the system during the surgical procedure. More particularly, rate of movement of a surgical instrument in instrument space in response to user input at a user input command device in user space is scaled based upon at least in part upon user skill level. For example, a record of the surgeon's skill level may indicate a novice skill level in performance of a needle driving surgical activity using a Large Suture Cut Needle Driver surgical instrument. In accordance with some embodiments, during the performance of the needle driving surgical activity, the instrument actuator is operated in a first (novice) mode in which the Large Suture Cut Needle Driver automatically moves very deliberately (1:0.333 scaling) relative to the user intent when near the respective tissue. Thus, the processor 58 is configured for a novice user of the Large Suture Cut Needle Driver surgical instrument in which translation of user input movement to instrument movement is scaled to slow instrument movement. A one-unit movement in user space imparted at control inputs 36, 38 is kinematically translated to a 0.333 unit movement of the instrument in surgical instrument space. Alternatively, for example, a record of the surgeon's skill level may indicate an intermediate skill level in performance of the needle driving surgical activity using a Large Needle Driver surgical instrument. In accordance with some embodiments, during the performance of the needle driving surgical activity, the instrument actuator is operated in a second (intermediate) mode in which the Large Needle Driver moves deliberately in a 1:0.5 scale relative to the user intent when near the respective tissue. Thus, the processor 58 is configured for intermediate skill level user of the Large Needle Driver surgical instrument in which translation of user input movement to instrument movement is scaled to slow instrument movement. A one-unit movement in user space imparted at control inputs 36, 38 is kinematically translated to a 0.5 unit movement of the instrument in surgical instrument space. As yet another alternative, for example, a record of the surgeon's skill level may indicate an experienced skill level in performance of the needle driving surgical activity using the Mega Needle Driver surgical instrument. In accordance with some embodiments, during the performance of the needle driving surgical activity, the instrument actuator is operated in a third (experienced) mode in which the Mega Needle Driver moves in the same speed, 1:1 scale, relative to the user intent when near the respective tissue. Thus, the processor 58 is configured for an experienced skill level user of the Mega Needle Driver surgical instrument in which translation of user input movement to instrument movement is scaled to match instrument movement. A one-unit movement in user space imparted at control inputs 36, 38 is kinematically translated to a 1.0-unit movement of the instrument in surgical instrument space.

Figure 13:
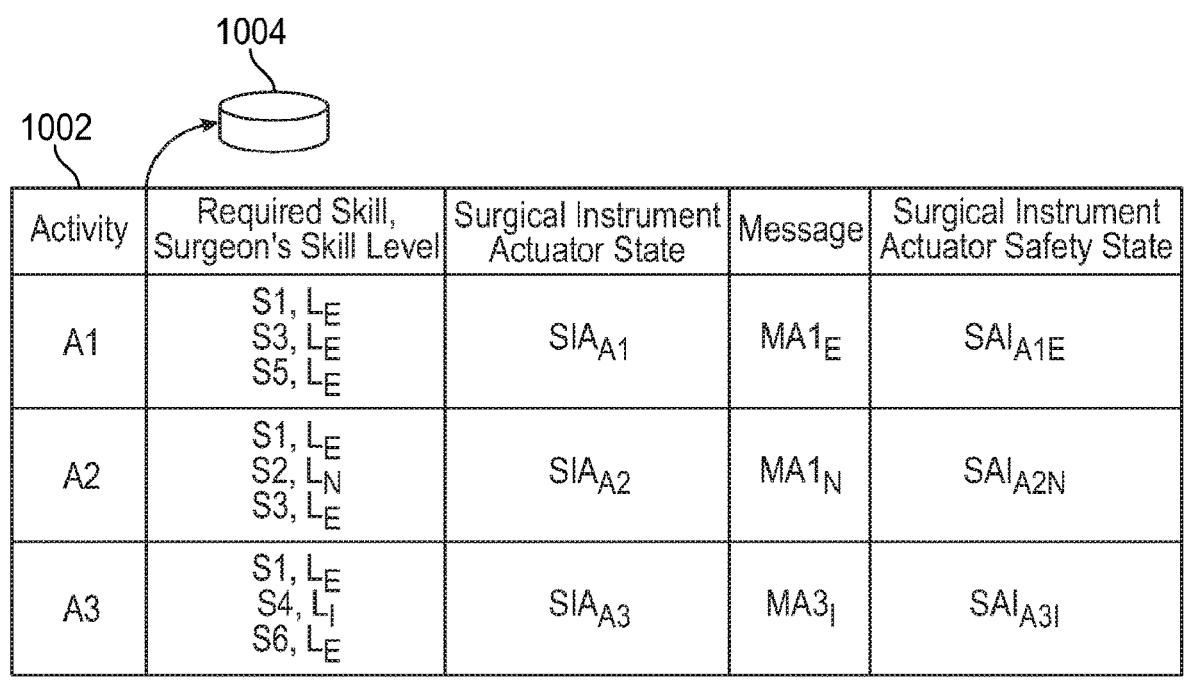
FIG. 13 is an illustrative drawing representing an example tenth information structure of the atlas stored in the computer readable storage device 1004 that corresponds to an example surgical procedure to be performed by an example surgeon.

FIG. 13 is an illustrative drawing representing an example tenth information structure 1020 of the atlas 1002 stored in the computer readable storage device 1004 that corresponds to an example surgical procedure to be performed by an example surgeon. The information structure 1020 associates surgical activities during the surgical procedure with surgeon skills. The information structure 1020 associates surgeon skills with a surgeon's skill levels. The information structure 1020 associates surgeon activities with surgical instrument actuator states. The information structure 1020 associates surgical state, surgical skill, surgical skill level, actuator state tuples with surgical actuator safety sates.

A first column of the information structure 1020 indicates a list of surgical activities, A1, A2 and A3 to be performed during the example surgical procedure. A second column of the information structure 1020 indicates lists of surgical skills required during each of the activities and corresponding skill levels of the surgeon performing the surgery for each of the skills. Specifically, in the example, activity A1 is associated with surgical skill S1, skill S3 and skill S5, and the surgeon possess an experienced skill level $L_E$ for all three skills S1, S2 and S5. Activity A2 is associated with surgical skills S1, S2, S3, and the surgeon possess an experienced skill level $L_E$ for skills S1 and S3 and S5 and possess a novice skill level $L_N$ for skill S2. Activity A3 is associated with surgical skills S1, S4, S6, and the surgeon possess an experienced skill level $L_E$ for skills S1 and S6 and possess an intermediate skill level L1 for skill S4. A third column of the information structure 1020 indicates surgical instrument actuation states indicative of the occurrence of the surgical activities. For example, surgical instrument actuator state $SIA_{A1}$ is indicative of occurrence of surgical state A1. Surgical instrument actuator state $SIA_{A2}$ is indicative of occurrence of surgical state A2. Surgical instrument actuator state $SIA_{A3}$ is indicative of occurrence of surgical state A3. A fourth column of the information structure 1020 indicates messages to be presented to a surgical team at different stages of a surgical procedure, based upon surgical activity states. For example, surgical activity state A1 is associated with message, $M_{A1E}$, directed to an experienced skill level surgeon; surgical activity state A2 is associated with message, $M_{A2N}$, directed to a novice skill level surgeon; and surgical activity state A3 is associated with message, $M_{A3I}$, directed to an intermediate skill level surgeon.

A fifth column of the information structure 1020 indicates surgical instrument actuator safety states to be used during different surgical activities of the surgical procedure. For example, surgical activity A1 is associated with an instrument actuator safety state $SAI_{A1E}$, which indicates that the surgeon has an experienced skill level for surgical activity A1. Surgical activity A2 is associated with an instrument actuator safety state $SIA_{A2N}$, which indicates that the surgeon has a novice skill level for surgical activity A2. Surgical activity A3 is associated with an instrument actuator safety state $SIA_{A3I}$, which indicates that the surgeon has intermediate skill level for surgical activity A3. It is noted that in this example, the associated instrument actuator safety state is at a level of the lowest corresponding surgeon skill level applicable for the surgical activity. For example, for activity A1, the surgeon's skill level is level $L_E$ (experienced) for all three skills S1, S3, S5, and therefore, the instrument actuator safety state is $SAI_{A1E}$, which corresponds to the experienced level. For activity A2, the surgeon's lowest skill level is level $L_N$ (novice) for skill S2, and therefore, the instrument actuator safety state is $SAI_{A21N}$, which corresponds to the novice level. For activity A3, the surgeon's lowest skill level is level $L_1$ (intermediate) for skill S4, and therefore, the instrument actuator safety state is $SAI_{A3I}$, which corresponds to the intermediate level.

Referring to the first row of the example information 1020 structure of FIG. 13, for example, during a surgical procedure involving, activity A1 of the surgery may involve tissue dissection, which requires skill S1=instrument wrist manipulation and orientation, skill S3=tissue grasping and manipulation, and skill S5=cutting. Message $MA1_E$ may indicate "to make small smooth cuts". Surgical instrument safety actuation state $A1_E$ may involve instrument is set to 1:1 scaling.

Referring to the second row of the example information 1020 structure of FIG. 13, for example, during the surgical procedure involving, activity A 2 of the surgery may involve tissue suturing, which requires skill S1, skill S2=needle driving and skill S3. Message $MA2_N$ may indicate "to be careful with needle handling to avoid unnecessary tissue needle piercings". Surgical instrument safety actuation state $A2_N$ may involve instrument is set to 1:0.333 scaling.

Referring to the third row of the example information 1020 structure of FIG. 13, for example, during the surgical procedure involving, activity A3 of the surgery may involve suture knot-tying, which requires skill S1, skill S4=suture handling and skill S6=knot-tying. Message $MA3_1$ may indicate "to be careful managing length of suture tail". Surgical instrument safety actuation state $A3_1$ may involve instrument is set to 1:0.5 scaling.

Figure 14:
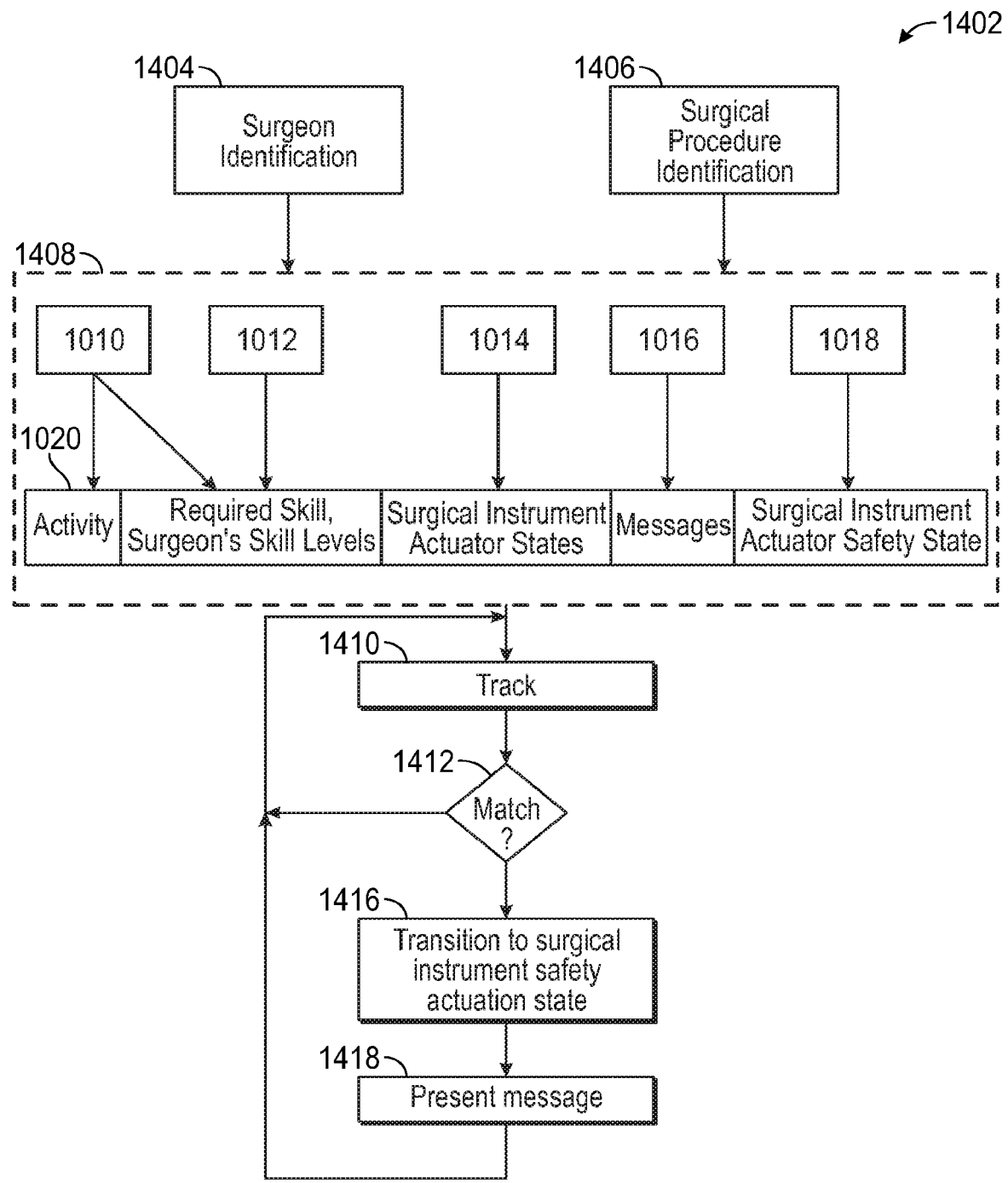
FIG. 14 is an illustrative flow diagram representing configuration of a processor to scale kinematic translation of user-to-instrument movement according to a surgical instrument safety actuation state based at least in part upon surgeon skill level information in accordance with some embodiments.

FIG. 14 is an illustrative flow diagram 1402 representing configuration of processor 58 to scale kinematic translation of user-to-instrument movement according to a surgical instrument safety actuation state based at least in part upon surgeon skill level information in accordance with some embodiments. Computer program code is used in some embodiments to configure one or more CPUs of the processor 58 to perform the process 1402. In block 1404, a surgeon identification is received at an input to a computer processing system associated with the electronics cart 56. In block 1406, an identification of a surgical procedure is received at an input of the computer processing system associated with the electronics cart 56. In block 1408, information included within the atlas 1002 within information structures 1010, 1012, 1014, 1016 and 1018 is used to produce an instance of the tenth information structure 1020 of FIG. 13 relating to the identified surgeon and to the identified surgical procedure.

During the performance of the identified surgical procedure, block 1410 tracks for each of one or more surgical instruments 26, which instrument is mounted in at a surgical instrument manipulator 512 and also tracks operational state of a surgical instrument actuator to determine, based upon the surgical instrument actuator state information within the third column of the produced instance of the tenth information structure 1020, when the surgical procedure is transitioning to an activity identified in the first column of the information structure 1020. In decision block 1412, a determination is made as to whether at least one of an instrument 26 mounted at a manipulator 512 a current instrument actuator state matches an actuator state associated with an activity. In response to no match, control loops back to block 1410 and tracking continues. In response to a match, block 1414 uses transitions the surgical instrument actuator to an instrument actuator safety state identified in the fifth column of the information structure 1020 that is associated with at least one of an instrument 26 mounted at a manipulator 512 and current instrument actuator state and an associated surgeon skill level indicated the second column of the information structure 1020. Block 1416 configures the display device 32, 34 and/or 60 to present to a surgical team a safety message associated with the current instrument actuator state and an associated surgeon skill level In some embodiments, control next flows back to block 1410, which continues to track surgical instrument actuator state based upon other identified actuator state transition information, for example.

Although illustrative embodiments have been shown and described, a wide range of modification, change and substitution is contemplated in the foregoing disclosure and in some instances, some features of the embodiments may be employed without a corresponding use of other features. For example, in some embodiments, a virtual surgical system comprises a first virtual robotic surgical instrument. The system includes an image generation device to produce images of virtual anatomical tissue and of the first virtual robotic surgical instrument. A user display is coupled to the image generation device so as to show to a user, the generated images of the virtual anatomical tissue and of the first virtual robotic surgical instrument. A user input command device is coupled to receive user input commands to control virtual movement of the first virtual robotic surgical instrument. A virtual movement controller is coupled to receive the user input commands from the input command device and configured to control virtual movement of the first virtual robotic surgical instrument in response to the user input commands and to scale a rate of virtual movement of the first virtual robotic surgical instrument, based at least in part upon a surgical skill level at using the first virtual robotic surgical instrument of the user providing the received user input commands, from a rate of movement indicated by the user input commands received at the user input command device.

Moreover, in some embodiments, a method is provided to operate a virtual surgical system that includes a virtual robotic surgical instrument manipulator. The method includes receiving user input commands from a user to control movement of a virtual robotic surgical instrument mounted at the virtual robotic surgical instrument manipulator. The method further includes determining an identification of a virtual robotic surgical instrument mounted at the virtual robotic surgical instrument manipulator during the receiving the user input commands. The method also includes scaling a rate of movement of the virtual robotic surgical instrument, based at least in part upon a skill level of the user at use of the identified virtual surgical instrument, from a rate of movement indicated by the user input commands. One of ordinary skill in the art would recognize many variations, alternatives, and modifications. Thus, the scope of the disclosure should be limited only by the following claims, and it is appropriate that the claims be construed broadly and in a manner consistent with the scope of the embodiments disclosed herein.

What is claimed is:

1. A surgical system comprising:
one or more processors, coupled to memory, and configured to:
identify a surgical instrument mounted to the surgical system, the surgical instrument moved by operation of a surgical instrument actuator;
determine based at least on a state of the surgical instrument actuator, that a surgical procedure is transitioning to a surgical activity of one or more surgical activities;
identify a surgical skill level of a surgeon at using the surgical instrument; and
match, via one or more information structures, the state of the surgical instrument actuator to an actuator state associated with the surgical activity, a safety state and the surgical skill level;
transition, responsive to the match, the state of the surgical instrument actuator to the safety state identified based at least on the surgical skill level of the surgeon.

2. The surgical system of claim 1, wherein the one or more processors are further configured to determine the safety state based at least on the surgical instrument, the state of the surgical instrument actuator and the surgical skill level of the surgeon for the surgical activity.

3. The surgical system of claim 1, wherein the one or more processors are further configured to transition the state of the surgical instrument actuator to the safety state, among a plurality of safety states, that matches the surgical skill level of the surgeon.

4. The surgical system of claim 1, wherein the one or more processors are further configured to match the state of the surgical instrument actuator to an actuator state associated with the surgical activity.

5. The surgical system of claim 1, wherein the one or more processors are further configured to identify from a record the surgical skill level of the surgeon associated with the surgical activity.

6. The surgical system of claim 1, wherein the one or more processors are further configured to scale kinetic translation of the surgeon to surgical instrument movement according to the safety state and the surgeon skill level.

7. The surgical system of claim 1, wherein the one or more processors are further configured to scale a rate of movement of the surgical instrument relative to a rate of movement of control input from the surgeon, based at least in part upon the surgical skill level of the surgeon.

8. The surgical system of claim 1, wherein the one or more processors are further configured to identify that the surgical instrument in mounted in a surgical instrument manipulator of the surgical system.

9. A surgical system comprising:
one or more processors, coupled to memory, and configured to:
receive identification of a surgeon and a surgical procedure;
identify a surgical instrument being controlled by operation of a surgical instrument actuator;
identify, via one or more information structures, a match between a surgical skill level of a surgical skill for a surgical activity of the surgical procedure and a surgical instrument actuator state and a surgical instrument actuator safety state; and
transition, responsive to determining the surgical procedure is transitioning to the surgical activity, the surgical instrument actuator state of the surgical instrument actuator to a surgical instrument actuator safety state based at least on the surgical skill level of the surgeon for the surgical skill for the surgical activity.

10. The surgical system of claim 9, wherein the one or more processors are further configured to determine based at least on a state of the surgical instrument actuator, that the surgical procedure is transitioning to the surgical activity of one or more surgical activities.

11. The surgical system of claim 9, wherein the one or more processors are further configured to identify from a record that the surgical instrument is mounted in a surgical instrument manipulator of the surgical system.

12. The surgical system of claim 9, wherein the one or more processors are further configured to transition the surgical instrument actuator state of the surgical instrument actuator to the surgical instrument actuator safety state based at least on the surgical skill level of the surgeon for the surgical skill for the surgical activity and a current state of the surgical instrument actuator.

13. The surgical system of claim 9, wherein the one or more processors are further configured to transition the surgical instrument actuator state of the surgical instrument actuator to the surgical instrument actuator safety state based at least on the surgical skill level of the surgeon for the surgical skill for the surgical activity and the surgical instrument.

14. The surgical system of claim 9, wherein the one or more processors are further configured to identify an information structure in a storage that provides the association.

15. A computer-implement method comprising:
identifying, by one or more processors, a surgical instrument mounted to a surgical system and a surgical skill level of a surgeon at using the surgical instrument, the surgical instrument moved by operation of a surgical instrument actuator;
determining, by the one or more processors based at least on a state of the surgical instrument actuator, that a surgical procedure is transitioning to a surgical activity of one or more surgical activities; and
matching, via one or more information structures, the state of the surgical instrument actuator to an actuator state associated with the surgical activity, a safety state and the surgical skill level; and
transitioning, by the one or more processors responsive to the matching, the state of the surgical instrument actuator to a safety state identified based at least on the state of the surgical instrument actuator and the surgical skill level of the surgeon.

16. The computer-implemented method of claim 15, further comprising scaling, by the one or more processors, a rate of movement of the surgical instrument relative to a rate of movement of control input from the surgeon, based at least in part upon the surgical skill level of the surgeon.

17. The computer-implemented method of claim 15, further comprising determining, by the one or more processors, the safety state based at least on the surgical instrument, the current state of the surgical instrument actuator and the surgical skill level of the surgeon for the surgical activity.

18. The computer-implemented method of claim 15, further comprising scaling, by the one or more processors, kinetic translation of the surgeon to surgical instrument movement according to the safety state and the surgeon skill level.

* * * * *